United States Patent
Tasaki et al.

(10) Patent No.: US 10,188,737 B2
(45) Date of Patent: Jan. 29, 2019

(54) STABILIZED PHARMACEUTICAL COMPOSITION

(71) Applicant: ASTELLAS PHARMA INC., Tokyo (JP)

(72) Inventors: Hiroaki Tasaki, Tokyo (JP); Mitsuru Yoshida, Tokyo (JP); Daisuke Tsunashima, Tokyo (JP); Ryota Azuma, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 0 days.

(21) Appl. No.: 15/569,057

(22) PCT Filed: Apr. 26, 2016

(86) PCT No.: PCT/JP2016/063004
§ 371 (c)(1),
(2) Date: Oct. 24, 2017

(87) PCT Pub. No.: WO2016/175192
PCT Pub. Date: Nov. 3, 2016

(65) Prior Publication Data
US 2018/0133325 A1  May 17, 2018

(30) Foreign Application Priority Data

Apr. 27, 2015 (JP) .................................. 2015-090702
Dec. 25, 2015 (JP) .................................. 2015-252958

(51) Int. Cl.
| | | |
|---|---|---|
| *A61K 31/497* | (2006.01) | |
| *A61K 47/26* | (2006.01) | |
| *A61K 47/36* | (2006.01) | |
| *A61K 47/38* | (2006.01) | |
| *A61K 9/48* | (2006.01) | |
| *A61K 47/02* | (2006.01) | |

(52) U.S. Cl.
CPC ............... *A61K 47/26* (2013.01); *A61K 9/48* (2013.01); *A61K 9/4816* (2013.01); *A61K 31/497* (2013.01); *A61K 47/02* (2013.01); *A61K 47/36* (2013.01); *A61K 47/38* (2013.01)

(58) Field of Classification Search
CPC .................................................... C07D 241/12
USPC ..................................................... 514/252.1
See application file for complete search history.

(56) References Cited

U.S. PATENT DOCUMENTS

| | | | |
|---|---|---|---|
| 9,085,540 B2 * | 7/2015 | Matsuya | ............. C07D 403/12 |
| 2014/0323463 A1 | 10/2014 | Matsuya et al. | |

FOREIGN PATENT DOCUMENTS

| | | |
|---|---|---|
| EP | 3150206 A1 | 4/2017 |
| JP | 2006-045218 A | 2/2006 |
| JP | 2013-245161 A | 12/2013 |
| WO | 2013/108754 A1 | 7/2013 |
| WO | 2015/182628 A1 | 12/2015 |

OTHER PUBLICATIONS

Drug Topics, 2008, pp. 1-12.*
7, Seizai no Kihon Mondai, Yakuzaigaku Manual, Nanzando Co., Ltd., Mar. 20, 1989; 107-108, 122, '7-1. Iyakuhin Tenkabutsu', '7-6. Iyakuhin no Rekka to sono Boshi.
1. Kyushitsu ni yoru Kagaku Henka, Funtai o Chushin to Shita Seizaigaku, 4th Ed., Hirokawa Shoten, Mar. 25, 1976; 233-236; whole article.
Osamu Shinozaki; "Suibun Sokutei Sochi", Pharmacia, 1983.09; 19(9), 900-902, particularly p. 900, column of Hajimeni, p. 902, column of Owarini.
Nyuto Suiwabutsu, Iyakuhin Tenkabutsu Jiten, 2007, Yakuji Nippo Ltd; Jul. 25, 2007; p. 204, whole article.
Yoto Betsu ni Mita Kobunshi Kagobutsu, Jitsuyo Iyakuhin Tenkabutsu, Kagaku Kogyosha, Mar. 5, 1974; pp. 104-105; particularly p. 105, upper part.
International Search Report; PCT/JP2016/063004 dated Jun. 30, 2016.
Heidemann, et al; Preformulation Studies Involving Moisture Uptake in Solid Dosage Forms; Pharmaceutical Research, vol. 8, No. 3, 1991.
Rajabi-Siahboomi, et al; Excipient Selection in Oral Solid Dosage Formulations Containing Moisture Sensitive Drugs; Excipient Applications in Formulation Design and Drug Delivery; Springer, 2013, pp. 385-421.
European Patent Office; Communication of Supplementary European Search Report of EP Application No. 16786469; dated Dec. 3, 2018.

* cited by examiner

*Primary Examiner* — Rei Tsang Shiao
(74) *Attorney, Agent, or Firm* — Kilpatrick Townsend & Stockton LLP

(57) ABSTRACT

Provided is a pharmaceutical composition, which comprises 5-{[(3R)-1-acryloylpyrrolidin-3-yl]oxy}-6-ethyl-3-({4-[4-(4-methylpiperazin-1-yl)piperidin-1-yl]phenyl}amino)-pyrazine-2-carboxamide (hereinafter referred to as "compound A") or a pharmaceutically acceptable salt thereof, and is stabilized. The pharmaceutical composition comprises compound A or a pharmaceutically acceptable salt thereof, and a pharmaceutical additive having a difference in water activity value of 0.1 or more, and is stabilized.

12 Claims, 1 Drawing Sheet

STABILIZED PHARMACEUTICAL COMPOSITION

CROSS-REFERENCE TO RELATED APPLICATIONS

The present application is a § 371 National Phase Application of PCT/JP2016/063004, filed Apr. 26, 2016, which application claims priority to JP 2015-252958, filed Dec. 25, 2015, and JP 2015-090702, filed Apr. 27, 2015, the disclosures of which are hereby incorporated by reference in their entireties for all purposes.

TECHNICAL FIELD

The present invention relates to a pharmaceutical composition, which comprises 5-{[(3R)-1-acryloylpyrrolidin-3-yl]oxy}-6-ethyl-3-({4-[4-(4-methylpiperazin-1-yl)piperidin-1-yl]phenyl}amino)-pyrazine-2-carboxamide, or a pharmaceutically acceptable salt thereof, and is stabilized.

BACKGROUND ART

5-{[(3R)-1-Acryloylpyrrolidin-3-yl]oxy}-6-ethyl-3-({4-[4-(4-methylpiperazin-1-yl)piperidin-1-yl]phenyl}amino)-pyrazine-2-carboxamide (hereinafter sometimes referred to as "compound A") is a compound represented by the following chemical structural formula. Compound A or a pharmaceutically acceptable salt thereof is known to be useful as an active ingredient of a pharmaceutical composition for treating cancer (Patent literature 1).

[Chem. 1]

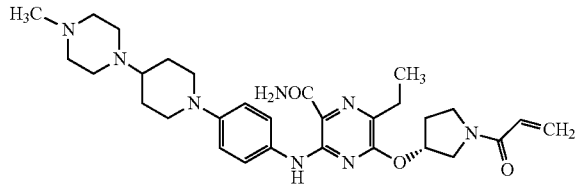

As compound A or a pharmaceutically acceptable salt thereof, Patent literature 1 discloses its free form in Example 54, and its monomethanesulfonate in Example 261, and discloses that the inhibitory action on an epidermal growth factor receptor (EGFR) mutant kinase has been confirmed.

Even today, in which the advancement of medical care is remarkable, especially for cancer, treatment satisfaction is low, and the contribution of further medicines is required. Providing stable medicines to medical professionals and people who need treatment of diseases and illness plays an important role contributing to the health of people around the world.

There are various destabilization mechanisms of drugs. There is a problem with the stability of the drug itself; in a pharmaceutical composition, particularly in a solid pharmaceutical composition, for example, there is a problem in the interaction between a drug and various pharmaceutical additives, or there are causes of instability of a drug in the manufacturing process; in a pharmaceutical composition, a drug reacts with moisture contained in pharmaceutical additives or the like (for example, Patent literatures 2 and 3); and the like. As described above, in terms of the nature of pharmaceuticals, it is extremely important to inhibit the generation of related substances, or the increase in the amount of related substances. However, a general method has not been established for the stabilization of drugs, and even at present, it has been sought for stabilizing a manner suitable for each drug.

CITATION LIST

Patent Literature

[Patent literature 1] WO 2013/108754
[Patent literature 2] Japanese Unexamined Patent Publication (Kokai) No. 2006-45218
[Patent literature 3] Japanese Unexamined Patent Publication (Kokai) No. 2013-245161

SUMMARY OF INVENTION

Technical Problem

A problem of the present invention is to provide a pharmaceutical composition, which comprises compound A or a pharmaceutically acceptable salt thereof, and is stabilized, for example, a pharmaceutical composition that is stable against humidity.

Solution to Problem

Despite the fact that compound A monomethanesulfonate is itself relatively stable, the inventors found that related substances and the amount of the related substances increased over time when a pharmaceutical composition (for example, capsules) containing the drug together with pharmaceutical additives was prepared by a conventional method, or via various formulation steps, and stored under severe conditions. Further, the inventors found that, when the measurement was carried out by "(Test for related substance)" described in Experimental Example 1 below, a related substance detected at a relative retention time to compound A of about 1.34 was the main related substance of compound A, and was a dimer of compound A; and the generation of the dimer was promoted by the moisture contained in the pharmaceutical additives in the pharmaceutical composition; and the like.

The dimer of compound A is represented by the following chemical structural formula.

[Chem. 2]

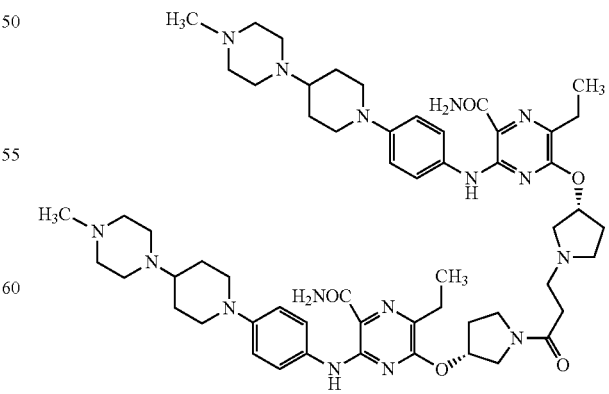

Under these circumstances, the inventors focused attention on the stability of compound A monomethanesulfonate under humidity conditions, and conducted intensive studies to complete the present invention.

The present invention relates to:

[1] a pharmaceutical composition, comprising 5-{[(3R)-1-acryloylpyrrolidin-3-yl]oxy}-6-ethyl-3-({4-[4-(4-methyl-piperazin-1-yl)piperidin-1-yl]phenyl}amino)-pyrazine-2-carboxamide, or a pharmaceutically acceptable salt thereof, and a pharmaceutical additive having a difference in water activity value of 0.1 or more,

[2] the pharmaceutical composition of [1], wherein the pharmaceutical additive having a difference in water activity value of 0.1 or more is one member, or two or more members selected from the group consisting of dextran, dextrin, crystalline cellulose, corn starch, calcium carbonate, lactose hydrate, anhydrous dibasic calcium phosphate, and mannitol,

[3] the pharmaceutical composition of [1] or [2], wherein the pharmaceutical additive having a difference in water activity value of 0.1 or more is lactose hydrate,

[4] the pharmaceutical composition of [2] or [3], wherein lactose hydrate is one member, or two or more members selected from the group consisting of sieved lactose, milled lactose, spray-dried lactose, and granulated lactose,

[5] the pharmaceutical composition of any one of [2] to [4], wherein lactose hydrate is spray-dried lactose,

[6] the pharmaceutical composition of any one of [1] to [5], wherein the content of the pharmaceutical additive having a difference in water activity value of 0.1 or more is about 0.1% by weight to about 99.9% by weight with respect to the weight of the pharmaceutical composition,

[7] the pharmaceutical composition of any one of [1] to [6], wherein the water activity of the pharmaceutical composition is controlled,

[8] the pharmaceutical composition of any one of [1] to [7], wherein the pharmaceutical composition is a capsule,

[9] the pharmaceutical composition of any one of [1] to [8], wherein the increased amount of a related substance of 5-{[(3R)-1-acryloylpyrrolidin-3-yl]oxy}-6-ethyl-3-({4-[4-(4-methylpiperazin-1-yl)piperidin-1-yl]phenyl}amino)-pyrazine-2-carboxamide, or a pharmaceutically acceptable salt thereof is 0.05% or less,

[10] a method of stabilizing a pharmaceutical composition comprising 5-{[(3R)-1-acryloylpyrrolidin-3-yl]oxy}-6-ethyl-3-({4-[4-(4-methylpiperazin-1-yl)piperidin-1-yl]phenyl}amino)-pyrazine-2-carboxamide, or a pharmaceutically acceptable salt thereof, by using a pharmaceutical additive having a difference in water activity value of 0.1 or more,

[11] a pharmaceutical composition comprising 5-{[(3R)-1-acryloylpyrrolidin-3-yl]oxy}-6-ethyl-3-({4-[4-(4-methyl-piperazin-1-yl)piperidin-1-yl]phenyl}amino)-pyrazine-2-carboxamide, or a pharmaceutically acceptable salt thereof, and lactose,

[12] the pharmaceutical composition of [11], wherein lactose is one member, or two or more members selected from the group consisting of sieved lactose, milled lactose, spray-dried lactose, and granulated lactose,

[13] the pharmaceutical composition of [11] or [12], wherein lactose is spray-dried lactose,

[14] the pharmaceutical composition of any one of [11] to [13], wherein the water activity of the pharmaceutical composition is controlled, and

[15] the pharmaceutical composition of any one of [11] to [14], wherein the pharmaceutical composition is a capsule.

Advantageous Effects of Invention

According to the present invention, a pharmaceutical composition, which comprises compound A or a pharmaceutically acceptable salt thereof, and is stabilized, for example, a pharmaceutical composition that is stable against humidity, can be provided.

DESCRIPTION OF EMBODIMENTS

Figure 1:
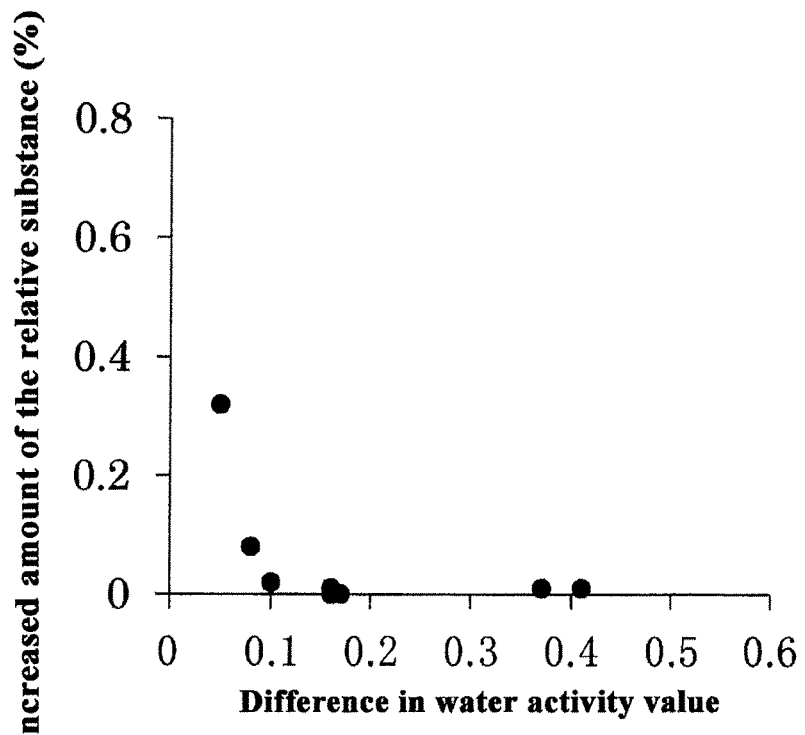
FIG. 1 is a graph showing the relationship between the increased amount of the related substance under storage conditions of 25° C. in Experimental Example 3 (Table 6) and the difference in water activity value in Experimental Example 4 (Table 7).

The term "to be stabilized" or "stabilization of a pharmaceutical composition" as used herein means a state where compound A or a pharmaceutically acceptable salt thereof is stabilized in a pharmaceutical composition (formulation) including a pharmaceutical additive. The state can be evaluated, for example, calculating the amount (percentage, %) or the like of related substances over time, in comparison with that at the beginning of the test. As the index, it is defined as a stable state enough to provide it as a pharmaceutical composition in the medical field.

For example, with respect to the percentage of related substances, in which a change is observed due to the moisture contained in a pharmaceutical composition, for example, the pharmaceutical composition is allowed to stand under storage conditions of 40° C. and 75% relative humidity (hereinafter sometimes abbreviated as % RH) (opened, closed, or sealed) for 1 month, and the percentage of the related substances is measured by a high performance liquid chromatographic method (hereinafter sometimes abbreviated as an HPLC method). When the related substances are measured, for example, by "(Test for related substance)" described in Experimental Example 1 below, the related substance having a relative retention time to compound A of about 1.34 is defined as a dimer of compound A. The content of the dimer of compound A (the related substance of compound A or a pharmaceutically acceptable salt thereof) is calculated by measuring the peak areas of all related substances including the dimer of compound A (the related substance detected at a relative retention time of about 1.34) contained in the pharmaceutical composition by the HPLC method, and dividing the peak area of the dimer of compound A by the total peak area of compound A or a pharmaceutically acceptable salt thereof and its related substances.

The term "to improve the stability of compound A or a pharmaceutically acceptable salt thereof" as used herein means that, when the pharmaceutical composition containing compound A or a pharmaceutically acceptable salt thereof is stored, "the generation of related substances of compound A or a pharmaceutically acceptable salt thereof during storage is inhibited".

With respect to the conditions for stability test, instead of the above-mentioned conditions of 40° C. and 75% RH (opened, closed, or sealed) for 1 month, the same conditions except that the storage period is 2 months, 3 months, or 6 months can be used. Further, the conditions of 25° C. and 60% RH (opened, closed, or sealed) can be appropriately combined with a storage period selected from 1 month to 24 months, or to 36 months. Furthermore, in order to evaluate for a short period of time, for example, the conditions of 70° C. for 9 days (opened, closed, or sealed conditions, such as aluminum-aluminum (Al-Al)-packaging and closed conditions) can be used. In this case, with respect to evaluation of "to be stable" as used herein, for example, a method that is judged to be scientifically valid, such as an extrapolation method, may be used, so that the conditions thermodynamically correspond to the result under storage conditions at 40° C. for 6 months.

The related substance in which a change is observed due to the moisture is defined, for example, as the dimer of compound A (the related substance having a relative retention time to compound A of about 1.34) under the measuring conditions for the HPLC method described in "(Test for related substance)" described in Experimental Example 1 below. Stability evaluation can be carried out by an absolute evaluation, in which the amount of the related substance is evaluated over time, or a relative evaluation, in which the amount of the related substance at the beginning of the test is compared with that at the time of the measurement. "To be stable" means that the increased amount of the dimer of compound A (the related substance detected at a relative retention time of about 1.34) after 1 month or 3 months from the beginning of the test for a relative evaluation is about 0.05% or less in an embodiment.

The total amount of related substances of compound A or a pharmaceutically acceptable salt thereof is measured, for example, by an HPLC method, after storing the pharmaceutical composition of 40° C. and 75% RH (opened, closed, or sealed) for 1 month.

The term "inhibition of the generation of the related substances", "inhibition of the increase in the amount of the related substances" or "improvement of stability" can be regarded as the same meaning as the above "stabilized" state.

The term "water activity" (sometimes abbreviated as "aw") as used herein is defined as a ratio of a water vapor pressure (P) in a closed container into which a substance to be measured is put to a vapor pressure (PO) of pure water at the temperature, and can be calculated by the following equation:

$$aw=P/PO$$

The water activity of pure water is 1.000 aw, and the water activity is expressed in the range of 0.000 to 1.000 aw.

The term "control of water activity" as used herein means that the water activity of the pharmaceutical composition is lowered, and adjusted so that it falls within the range of a specific water activity value. For example, an addition of a pharmaceutical additive so that the difference in water activity value falls within a specific range; drying of the pharmaceutical composition; a use of a desiccant in a packaging form; and a method in which the above pharmaceutical additive is dried using a desiccant or the like, and the dried pharmaceutical additive is used as an additive or the like for the pharmaceutical composition; may be exemplified.

The term "difference in water activity value" as used herein means a difference between a water activity value of a pharmaceutical additive under humidity conditions and a water activity value of the pharmaceutical additive in a dry state. It can be determined, for example, by the method described in Experimental Example 4 below. Since the larger the difference in water activity value, the larger the amount of water adsorption under humidity conditions; or since the amount of water desorption increases by the use of a desiccant; or the like, it is considered that the stability of compound A monomethanesulfonate under humidity conditions is improved.

The term "about" as used herein means, when it is used in connection with numerical variables, a larger variable value, in general, within an experimental error (for example, within the 95% confidence interval for the mean), or within ±10% of the indicated value, and all the values of the variable.

The pharmaceutical composition of the present invention will be explained below.

Compound A or a pharmaceutically acceptable salt thereof, which is used in the present invention, is easily available, for example, by a method described in Patent literature 1, or in a similar fashion to that.

Compound A may be in a free form in an embodiment, and may form a pharmaceutically acceptable salt with an acid in other embodiments. Examples of such a salt include an acid addition salt with an inorganic acid, such as hydrochloric acid, hydrobromic acid, hydroiodic acid, sulfuric acid, nitric acid, phosphoric acid, or the like; and an acid addition salt with an organic acid, such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid (mesylic acid), ethanesulfonic acid, benzenesulfonic acid, p-toluenesulfonic acid, aspartic acid, glutamic acid, or the like. "Compound A or a pharmaceutically acceptable salt" includes solvates of compound A, in particular, such as hydrates or ethanol solvates, as well as solvates of an acid addition salt of compound A. In an embodiment, it is 5-{[(3R)-1-acryloylpyrrolidin-3-yl]oxy}-6-ethyl-3-({4-[4-(4-methylpiperazin-1-yl)piperidin-1-yl]phenyl}amino)-pyrazine-2-carboxamide monomethanesulfonate.

These salts can be prepared by conventional methods.

For ordinary oral administration, the daily dose is suitably about 0.001 to 100 mg/kg in an embodiment, 0.1 to 30 mg/kg in another embodiment, and 0.1 to 10 mg/kg in still another embodiment, and this is administered in one dose, or divided into 2 to 4 doses per day. The dose may be appropriately determined according to individual cases in consideration of the symptoms, age, sex, and the like.

The content of compound A or a pharmaceutically acceptable salt thereof is, for example, per pharmaceutical composition, about 0.1% by weight or more and about 99.9% by weight or less in an embodiment, and about 4% by weight or more and about 50% by weight or less in an embodiment.

The "pharmaceutical additive having a difference in water activity value of 0.1 or more", which is used in the present invention, is defined as a substance in which a difference in water activity value measured under the conditions as described in Experimental Example 4 below is 0.1 or more, and 0.1 or more and 0.5 or less in an embodiment. More particular, examples of the pharmaceutical additive having a difference in water activity value of 0.1 or more include dextran, dextrin, crystalline cellulose, corn starch, calcium carbonate, lactose hydrate, anhydrous dibasic calcium phosphate, mannitol, and the like. In an embodiment, it is lactose hydrate.

The pharmaceutical additive having a difference in water activity value of 0.1 or more can be used alone, or as an appropriate combination of two or more.

Lactose hydrate, which is used in the present invention, is not particularly limited, so long as it is lactose hydrate that is acceptable as a pharmaceutical additive. More particularly, examples of lactose hydrate include sieved lactose, milled lactose, spray-dried lactose, granulated lactose, and the like. It is spray-dried lactose in an embodiment. Examples of spray-dried lactose include SuperTab 11SD (DFE Pharma), and the like.

Lactose hydrate can be used alone, or as an appropriate combination of two or more.

With respect to lactose hydrate, the generation of related substances other than a dimer of compound A (a relative retention time is about 1.34), which is newly generated in the formulation process, is not observed, and a stable pharmaceutical composition can be provided.

The amount of the "pharmaceutical additive having a difference in water activity value of 0.1 or more" is not particularly limited, so long as it is an amount that constitutes a formulation comprising compound A or a pharmaceutically acceptable salt thereof in the pharmaceutical composition (formulation). More particularly, the content is, for example, per pharmaceutical composition, about 0.1% by weight or more and about 99.9% by weight or less, about 50% by weight or more and about 99% or less in an embodiment, and about 50% by weight or more and about 96% or less in an embodiment.

The water activity value in the pharmaceutical composition of the present invention is not particularly limited, so long as the water activity value is enough to maintain a state in which the pharmaceutical composition comprising compound A or a pharmaceutically acceptable salt thereof is stabilized under severe conditions. More particularly, it is, for example, about 0.6 or less, about 0.35 or less in an embodiment, and about 0.1 or less in an embodiment. In the pharmaceutical composition comprising compound A or a pharmaceutically acceptable salt thereof, the lower the water activity value of the whole composition, and/or, the larger difference in water activity value the pharmaceutical additives have, the more strongly the generation of the related substances in the pharmaceutical composition is inhibited, and it is preferable from the viewpoint of chemical stability.

The method of controlling or adjusting water activity is not particularly limited, so long as it is a method of lowering the moisture retained by the pharmaceutical composition. For example, an addition of a pharmaceutical additive so that the difference in water activity value falls within a specific range; drying of the pharmaceutical composition; a use of a desiccant in a packaging form; and a method in which the above pharmaceutical additive is dried using a desiccant or the like, and the dried pharmaceutical additive is used as an additive or the like for the pharmaceutical composition; may be exemplified. In an embodiment, an addition of a pharmaceutical additive so that the difference in water activity value falls within a specific range, may be exemplified. The desiccant, in particular, the type, performance, and amount, is not particularly limited, but the desiccant with higher water absorption capacity obtains the greater effect. Examples of the desiccant include silica gel desiccants, zeolite desiccants, active carbon desiccants, and the like. The form of the desiccant is not particularly limited. For example, in the case of bottle packaging, a type attached to the back of a lid, and a type to be introduced into a bottle may be exemplified, and in the case of PPT packaging, a sheet type may be exemplified.

In the pharmaceutical composition of the present invention, it is suggested that the larger difference in water activity value the pharmaceutical additives have, the more strongly the generation of the related substances is inhibited, and it is preferable from the viewpoint of chemical stability.

The pharmaceutical composition of the present invention may be various pharmaceutical compositions (formulations), such as tablets, capsules, granules, powder, fine granules, and the like. In an embodiment, it may be a capsule.

In the pharmaceutical composition of the present invention, it may be formulated by appropriately using various pharmaceutical additives, if desired, to the extent that the desired effects of the present invention can be achieved. Such pharmaceutical additives are not particularly limited, so long as they are pharmaceutically acceptable and pharmacologically acceptable. Examples of the pharmaceutical additives include a filler, a lubricant, a fluidizing agent, a binder, a disintegrating agent, an effervescent agent, a sweetener, a flavor, a colorant, a surfactant, and the like.

Examples of the lubricant include magnesium stearate, and the like.

These pharmaceutical additives may be appropriately added alone, or as a combination of two or more, in appropriate amounts.

With respect to the contents of the pharmaceutical additives, each pharmaceutical additive may be contained in an amount such that the desired effects of the present invention may be achieved.

The process of manufacturing the pharmaceutical composition of the present invention will be explained below.

The pharmaceutical composition of the present invention can be prepared by methods known per se.

More particularly, the process includes various manufacturing processes, such as pulverization of compound A or a pharmaceutically acceptable salt thereof, mixing, filling, if necessary, granulation, compression, drying, packaging, and the like.

The present invention includes a method of stabilizing a pharmaceutical composition comprising compound A or a pharmaceutically acceptable salt thereof, by using a pharmaceutical additive having a difference in water activity value of 0.1 or more.

With respect to "compound A or a pharmaceutically acceptable salt thereof" and the "pharmaceutical additive having a difference in water activity value of 0.1 or more", which are used in the stabilizing method of the present invention, the explanations therefor described in the pharmaceutical composition of the present invention can be directly applied.

According to the stabilizing method of the present invention, when the pharmaceutical composition comprising compound A or a pharmaceutically acceptable salt thereof and the pharmaceutical additive having a difference in water activity value of 0.1 or more is prepared, the generation of related substances (in particular, related substances in which a change is observed due to the moisture contained in the pharmaceutical composition) can be inhibited by adding the pharmaceutical additive having a difference in water activity value of 0.1 or more.

With respect to the content of each component, the mixing of the components, and the like, in the stabilizing method of the present invention, the explanations therefor described in the pharmaceutical composition of the present invention can be directly applied.

EXAMPLES

The present invention will now be further illustrated by, but is by no means limited to, the following Examples and Experimental Examples.

Compound A monomethanesulfonate, which was used in the Examples below, had been prepared in accordance with a method described in WO 2013/108754.

Examples 1 to 3

After compound A monomethanesulfonate was pulverized, a mixture obtained by mixing it with lactose hydrate, in accordance with the components and the contents as shown in Table 1, was sieved through a sieve, and if necessary, magnesium stearate was further added, and mixed again. The obtained mixture was filled into hypromellose capsules to prepare a pharmaceutical composition (capsules) of the present invention. In connection with this, milled lactose (Pharmatose 200M, DFE Pharma) was used in Examples 1 and 2, and spray-dried lactose (SuperTab 11SD, DFE Pharma) was used in Example 3.

TABLE 1

|  | Example 1 | Example 2 | Example 3 |
|---|---|---|---|
| Compound A monomethanesulfonate | 4.3 | 10.5 | 41.8 |
| Lactose hydrate | 95.7 | 89.5 | 56.7 |
| Magnesium stearate | — | — | 1.5 |
| Total | 100 | 100 | 100 |
| Hypromellose capsule | 1 capsule | 1 capsule | 1 capsule |

(Unit: % by weight)

Experimental Example 1

After the capsules obtained in Example 3 were allowed to stand in various packaging forms, as shown in Table 2, under storage conditions of 40° C. and 75% RH for 3 months, the amount of a related substance (the amount of a dimer of compound A at a relative retention time of about 1.34) and the water activity value were measured to evaluate the stability of the capsule over time, in comparison with those at the beginning of the test.

(Test for Related Substance)

The amounts of generated related substances were measured by a high performance liquid chromatographic method (an HPLC method). The amount of a related substance is calculated by measuring the peak area of each related substance contained in a pharmaceutical composition by the HPLC method, and dividing the peak area of a dimer of compound A (a related substance detected at a relative retention time of about 1.34) by the total peak area of all related substances, including compound A or a pharmaceutically acceptable salt thereof and the dimer of compound A.

Measurement wavelength: 210 nm

Column: YMC-Triart C18 (4.6 mm×150 mm, 3 μm)

Column temperature: a constant temperature around 40° C.

Mobile phase: A mixed solution of 45 mM perchloric acid aqueous solution and acetonitrile Flow rate: about 1.2 mL/min.

Injection amount: 10 μg (corresponding to compound A)

(Measurement of Water Activity)

A water activity meter (AQUA LAB Series 4TE (AQUA LAB)) was used to measure the water activity value of each pharmaceutical composition (including a capsule shell) at 25° C.

(Results)

As apparent from the results shown in Table 2, with respect to the capsule (Al-Al blister) of Example 3, the generation of the related substance was inhibited and was stable. In the case where the water activity value was low at 25° C. (polyvinyl chloride (PVC) blister/Al pillow (desiccant)), the generation of the related substance was remarkably inhibited and was very stable.

TABLE 2

| Packaging form | Water activity value | Increased amount of related substance (versus initial), % | | |
|---|---|---|---|---|
|  |  | After 1 month | After 2 months | After 3 months |
| PVC blister/Al pillow (desiccant) | 0.07 | 0.01 | 0.02 | 0.01 |
| Al—Al blister | 0.34 | 0.03 | 0.05 | 0.07 |

Experimental Example 2

After 1.171 mg of compound A monomethanesulfonate and 98.829 mg of milled lactose hydrate (Pharmatose 200 M, DFE Pharma) were mixed, the obtained mixture was filled into hypromellose capsules. The filled capsules were put into plastic bottles, and the bottles were sealed and allowed to stand under storage conditions of 25° C. and 60% RH for 1 month. After the storage, the amount of a related substance (the amount of a dimer of compound A at a relative retention time of about 1.34) was measured under the same conditions as those of Experimental Example 1.

The difference between the amount of the related substance in the mixture stored at 25° C. and 60% RH for 1 month and the amount of the related substance of compound A monomethanesulfonate stored under storage conditions of 25° C. and 60% RH for 1 month was summarized in Table 3, as the increased amount of the related substance.

TABLE 3

|  | 25° C. · 60% RH After 1 month (%) | Increased amount of related substance (%) |
|---|---|---|
| Compound A Monomethanesulfonate (alone) | 0.44 | — |
| Mixture with lactose hydrate | 0.43 | −0.01 |

It was suggested that the mixture of compound A monomethanesulfonate and the milled lactose hydrate was stable.

Lactose exhibits a large difference between the water activity value under humidity conditions and the water activity value in a dry state, and it is considered that lactose contributes to the stabilization of compound A monomethanesulfonate under humidity conditions.

Examples 4 to 11

Pharmaceutical compositions of the present invention were obtained by mixing 117.1 mg of compound A monomethanesulfonate (corresponding to 100 mg of the free form), which had been allowed to stand under storage conditions of 25° C. and 60% RH (opened) for 3 days, with 5 g×2 bottles (total 10 g) of each pharmaceutical additive, as shown in Table 4, which had been allowed to stand in bottles (30 mL) at 25° C. for 3 days in the presence of a desiccant (2 g).

As the additives, dextran (dextran, Wako Pure Chemical Industries, Ltd.), dextrin (dextrin, Nacalai Tesque Inc.), crystalline cellulose (Ceolus PH 102, Asahi Kasei Chemicals), corn starch (corn starch, Nihon Shokuhin Kako Co., Ltd.), calcium carbonate (calcium carbonate, Kozakai Pharmaceutical Co., Ltd.), lactose hydrate, anhydrous dibasic calcium phosphate (GS, Kyowa Chemical Industry Co., Ltd.), and mannitol (Pearlitol 50C, Roquette Freres) were used.

TABLE 4

| | Example 4 | Example 5 | Example 6 | Example 7 | Example 8 | Example 9 | Example 10 | Example 11 |
|---|---|---|---|---|---|---|---|---|
| Compound A monomethanesulfonate | 117.1 | 117.1 | 117.1 | 117.1 | 117.1 | 117.1 | 117.1 | 117.1 |
| Dextran | 10000 | — | — | — | — | — | — | — |
| Dextrin | — | 10000 | — | — | — | — | — | — |
| Crystalline cellulose | — | — | 10000 | — | — | — | — | — |
| Corn starch | — | — | — | 10000 | — | — | — | — |
| Calcium carbonate | — | — | — | — | 10000 | — | — | — |
| Lactose hydrate | — | — | — | — | — | 10000 | — | — |
| Anhydrous dibasic calcium phosphate | — | — | — | — | — | — | 10000 | — |
| Mannitol | — | — | — | — | — | — | — | 10000 |
| Total | 10117.1 | 10117.1 | 10117.1 | 10117.1 | 10117.1 | 10117.1 | 10117.1 | 10117.1 |

(Unit: mg)

Comparative Examples 1 to 2

Pharmaceutical compositions for comparison were obtained by mixing 117.1 mg of compound A monomethanesulfonate (corresponding to 100 mg of the free form), which had been allowed to stand under storage conditions of 25° C. and 60% RH (opened) for 3 days, with 5 g×2 bottles (total 10 g) of each pharmaceutical additive, as shown in Table 5, which had been allowed to stand in bottles (30 mL) at 25° C. for 3 days in the presence of a desiccant (2 g).

TABLE 5

| | Comparative Example 1 | Comparative Example 2 |
|---|---|---|
| Compound A monomethanesulfonate | 117.1 | 117.1 |
| Sucrose | 10000 | — |
| Trehalose | — | 10000 |
| Total | 10117.1 | 10117.1 |

(Unit: mg)

Experimental Example 3

The mixtures obtained in Examples 4 to 11 and Comparative Examples 1 to 2, as well as compound A monomethanesulfonate, were put into plastic bottles. The bottles were sealed, and packaged using aluminum bags, and the aluminum bags were allowed to stand under storage conditions of 25° C. or 40° C. for 1 month. After the storage, the amount of a related substance (the amount of a dimer of compound A at a relative retention time of about 1.34) was measured under the same conditions as those of Experimental Example 1.

The difference between the amount of the related substance in each mixture stored at 25° C. or 40° C. for 1 month and the amount of the related substance of each compound A monomethanesulfonate stored under storage conditions of 25° C. or 40° C. for 1 month was summarized in Table 6, as the increased amount of the related substance.

TABLE 6

| | 25° C., After 1 month | | 40° C., After 1 month | |
|---|---|---|---|---|
| | Amount of related substance (%) | Increased amount of related substance (%) | Amount of related substance (%) | Increased amount of related substance (%) |
| Compound A monomethanesulfonate (alone) | 0.03 | — | 0.03 | — |
| Example 4 | 0.04 | 0.01 | 0.04 | 0.01 |
| Example 5 | 0.02 | −0.01 | 0.00 | −0.03 |
| Example 6 | 0.01 | −0.02 | 0.01 | −0.02 |
| Example 7 | 0.04 | 0.01 | 0.03 | 0.00 |
| Example 8 | 0.04 | 0.01 | 0.05 | 0.02 |
| Example 9 | 0.03 | 0.00 | 0.03 | 0.00 |
| Example 10 | 0.03 | 0.00 | 0.03 | 0.00 |
| Example 11 | 0.05 | 0.02 | 0.05 | 0.02 |
| Comparative Example 1 | 0.35 | 0.32 | 0.33 | 0.30 |
| Comparative Example 2 | 0.11 | 0.08 | 0.13 | 0.10 |

(N = 2)
* Since the quantitative limit of measurement is 0.05%, the values less than 0.05% are shown as reference values.

Experimental Example 4

Pharmaceutical additives (5000 mg each) used in Examples 4 to 11 and Comparative Examples 1 to 2 were allowed to stand in bottles (30 mL) at 25° C. for 3 days in the presence of a desiccant (2 g), and the water activity value was measured under the same conditions as those of Experimental Example 1. Further, the same samples were allowed to stand in bottles under storage conditions of 25° C. and 60% RH (opened) for 3 days, and the water activity value was measured under the same conditions as those of Experimental Example 1

The difference between the water activity value after the storage in the opened state and the water activity value after the storage in the sealed state is summarized in Table 7.

TABLE 7

| | Pharmaceutical additive | Water activity value | | |
|---|---|---|---|---|
| | | Opened | Sealed | Difference |
| Example 4 | Dextran | 0.46 | 0.05 | 0.41 |
| Example 5 | Dextrin | 0.43 | 0.03 | 0.40 |
| Example 6 | Crystalline cellulose | 0.57 | 0.15 | 0.42 |
| Example 7 | Corn starch | 0.57 | 0.20 | 0.37 |
| Example 8 | Calcium carbonate | 0.53 | 0.37 | 0.16 |

TABLE 7-continued

| | | Water activity value | | |
|---|---|---|---|---|
| | Pharmaceutical additive | Opened | Sealed | Difference |
| Example 9 | Lactose hydrate | 0.46 | 0.30 | 0.16 |
| Example 10 | Anhydrous dibasic calcium phosphate | 0.46 | 0.29 | 0.17 |
| Example 11 | Mannitol | 0.45 | 0.35 | 0.10 |
| Comparative Example 1 | Sucrose | 0.43 | 0.38 | 0.05 |
| Comparative Example 2 | Trehalose | 0.40 | 0.32 | 0.08 |

(N = 3)

Figure 2:
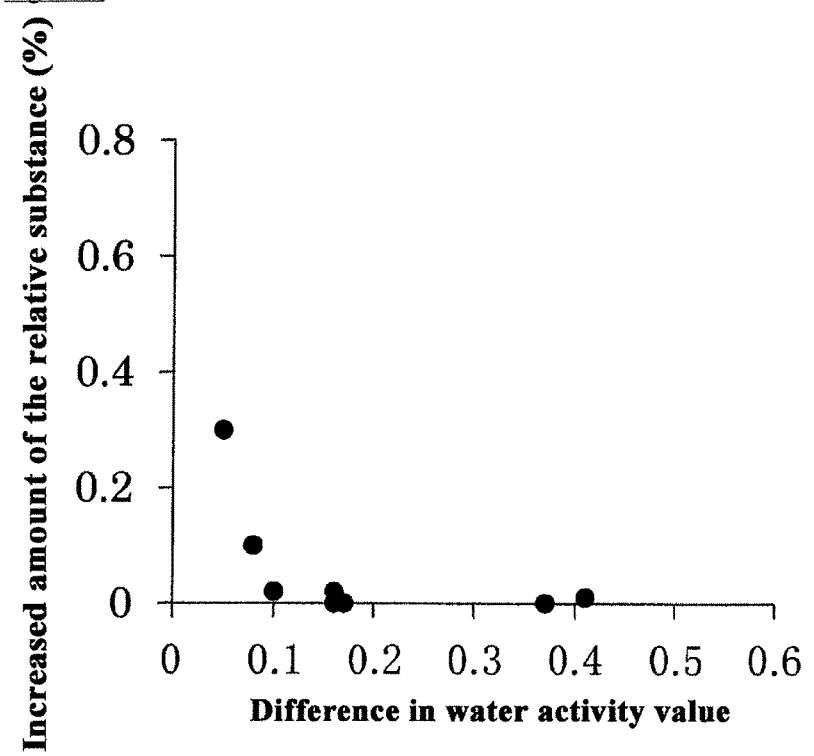
FIG. 2 is a graph showing the relationship between the increased amount of the related substance under storage conditions of 40° C. in Experimental Example 3 (Table 6) and the difference in water activity value in Experimental Example 4 (Table 7).

From the relationship between the increased amount of the related substance in Table 6 and the difference in water activity value in Table 7 (FIGS. 1 and 2), it is considered that the difference between the water activity value under the humidity condition and the water activity value in the dry state contributes to the stabilization of compound A monomethanesulfonate under humidity conditions. Further, it is suggested that a mixture of a pharmaceutical additive having a difference in water activity value of 0.1 or more and compound A monomethanesulfonate is stable.

INDUSTRIAL APPLICABILITY

The present invention is useful as a formulation technique for providing a stable pharmaceutical composition comprising compound A or a pharmaceutically acceptable salt thereof (such as, compound A monomethanesulfonate), for example, a pharmaceutical composition that is stable against humidity.

Although the present invention has been described with reference to specific embodiments, various changes and modifications obvious to those skilled in the art are possible without departing from the scope of the appended claims.

The invention claimed is:

1. A pharmaceutical composition, comprising 5-{[(3R)-1-acryloylpynolidin-3-yl]oxy}-6-ethyl-3-({4-[4-(4-methyl-piperazin-1-yl)piperidin-1-yl]phenyl}amino)-pyrazine-2-carboxamide, or a pharmaceutically acceptable salt thereof, and a pharmaceutical additive having a difference in water activity value of 0.1 or more, wherein the difference in water activity value is the water activity value difference between said pharmaceutical additive after storage in the opened state and said pharmaceutical additive after storage in the sealed state, and wherein the pharmaceutical additive having a difference in water activity value of 0.1 or more is one member, or two or more members selected from the group consisting of dextran, dextrin, crystalline cellulose, corn starch, calcium carbonate, lactose hydrate, anhydrous dibasic calcium phosphate, and mannitol.

2. The pharmaceutical composition according to claim 1, wherein the pharmaceutical additive having a difference in water activity value of 0.1 or more is lactose hydrate.

3. The pharmaceutical composition according to claim 1, wherein lactose hydrate is one member, or two or more members selected from the group consisting of sieved lactose, milled lactose, spray-dried lactose, and granulated lactose.

4. The pharmaceutical composition according to claim 1, wherein lactose hydrate is spray-dried lactose.

5. The pharmaceutical composition according to claim 1, wherein the content of the pharmaceutical additive having a difference in water activity value of 0.1 or more is about 0.1% by weight to about 99.9% by weight with respect to the weight of the pharmaceutical composition.

6. The pharmaceutical composition according to claim 1, wherein the water activity of the pharmaceutical composition is controlled.

7. The pharmaceutical composition according to claim 1, wherein the pharmaceutical composition is a capsule.

8. The pharmaceutical composition according to claim 1, wherein the increased amount of a related substance of 5-{[(3R)-1-acryloylpyrrolidin-3-yl]oxy}-6-ethyl-3-({4-[4-(4-methylpiperazin-1-yl)piperidin-1-yl]phenyl}amino)-pyrazine-2-carboxamide, or a pharmaceutically acceptable salt thereof is 0.05% or less.

9. A method of stabilizing a pharmaceutical composition comprising 5-{[(3R)-1-acryloylpyrrolidin-3-yl]oxy}-6-ethyl-3-({4-[4-(4-methylpiperazin-1-yl)piperidin-1-yl]phenyl}amino)-pyrazine-2-carboxamide, or a pharmaceutically acceptable salt thereof, by using a pharmaceutical additive having a difference in water activity value of 0.1 or more, wherein the difference in water activity value is the water activity value difference between said pharmaceutical additive after storage in the opened state and said pharmaceutical additive after storage in the sealed state, and wherein the pharmaceutical additive having a difference in water activity value of 0.1 or more is one member, or two or more members selected from the group consisting of dextran, dextrin, crystalline cellulose, corn starch, calcium carbonate, lactose hydrate, anhydrous dibasic calcium phosphate, and mannitol.

10. A pharmaceutical composition comprising 5-{[(3R)-1-acryloylpyrrolidin-3-yl]oxy}-6-ethyl-3-({4-[4-(4-methylpiperazin-1-yl)piperidin-1-yl]phenyl}amino)-pyrazine-2-carboxamide, or a pharmaceutically acceptable salt thereof, and lactose.

11. The pharmaceutical composition according to claim 1, wherein the pharmaceutical additive having a difference in water activity value of 0.1 or more is one member, or two or more members selected from the group consisting of dextran, dextrin, and anhydrous dibasic calcium phosphate.

12. The method of stabilizing a pharmaceutical composition of claim 9, wherein the pharmaceutical additive having a difference in water activity value of 0.1 or more is one member, or two or more members selected from the group consisting of dextran, dextrin, and anhydrous dibasic calcium phosphate.

* * * * *